United States Patent [19]

Glamkowski et al.

[11] 4,024,258

[45] May 17, 1977

[54] COMPOSITION OF AND METHOD FOR REDUCING HYPERTENSION WITH A 1-[1-(INDOL-3-YLETHYL)-PIPERAZIN-4-YL]-3-SUBSTITUTED UREA

[75] Inventors: Edward J. Glamkowski, Warren; Philip A. Reitano, Raritan, both of N.J.

[73] Assignee: American Hoechst Corporation, Bridgewater, N.J.

[22] Filed: Oct. 17, 1975

[21] Appl. No.: 623,337

Related U.S. Application Data

[62] Division of Ser. No. 475,316, May 31, 1974, Pat. No. 3,948,918.

[52] U.S. Cl. .............................................. 424/250
[51] Int. Cl.² ...................................... A61K 31/495
[58] Field of Search .................................... 424/250

[56] References Cited

UNITED STATES PATENTS

| 2,663,707 | 12/1953 | Conroy et al. | 260/268 N |
| 3,188,313 | 6/1955 | Archer | 260/268 BC |

Primary Examiner—Albert T. Meyers
Assistant Examiner—Daren M. Stephens
Attorney, Agent, or Firm—Curtis, Morris & Safford

[57] ABSTRACT

1-[1-(Indol-3-ylethyl)-piperazin-4-yl]-3-substituted urea compounds, their physiologically tolerable acid addition salts, and a process for the preparation thereof are described. The compounds are useful as antihypertensive agents.

10 Claims, No Drawings

COMPOSITION OF AND METHOD FOR REDUCING HYPERTENSION WITH A 1-[1-(INDOL-3-YLETHYL)-PIPERAZIN-4-YL]-3-SUBSTITUTED UREA

This is a division, of application Ser. No. 475,316 filed May 31, 1974, now U.S. Pat. No. 3,948,918.

This invention relates to 1-[1-(indol-3-ylethyl)-piperazin-4-yl]-3-substituted ureas, their physiologically tolerable acid addition salts and their method of preparation. These compounds have antihypertensive activity.

To the best of our knowledge, the compounds of this invention have not heretofore been described. Benzamidopiperidylethylindoles are reported to be potent hypotensive agents [J. L. Archibald, B. J. Alps, J. F. Caballo, and J. L. Jackson, J. Med. Chem., 14, 1054 (1971)], and 1-[(3-indolyl)]-4-arylpiperazines are reported to be active as central nervous system depressants [D. W. Wylie and S. Archer, J. Med. Pharm. Chem., 5, 932(1962)].

The compounds of the invention are represented by the formula:

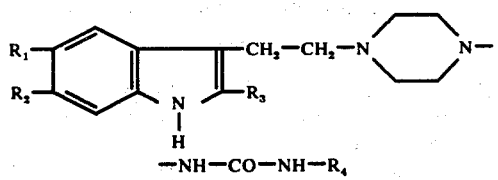
—NH—CO—NH—R$_4$ wherein R$_1$ and R$_2$ are hydrogen or alkoxy of from 1 to 3 carbon atoms; R$_3$ is hydrogen or alkyl of from 1 to 3 carbon atoms; and R$_4$ is alkyl of from 1 to 4 carbon atoms, cycloalkyl of from 3 to 8 carbon atoms, phenyl or phenyl mono-, di-, or tri-substituted by halogen, alkyl of from 1 to 3 carbon atoms, alkoxy of from 1 to 2 carbon atoms, trifluoromethyl or nitro; and the physiologically tolerable acid addition salts thereof. When R$_4$ is a substituted phenyl, the substituents can be on any of the five available positions of the benzene ring.

The compounds of the present invention are prepared by the addition of an isocyanate of the formula, R$_4$—N=C=O, wherein R$_4$ is as defined earlier, to a 3-[2-(4-aminopiperazin-1-yl)ethyl]indole of the formula:

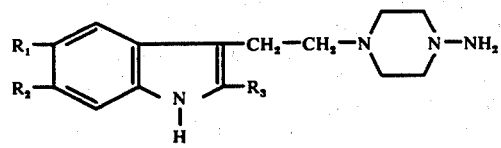

wherein R$_1$, R$_2$ and R$_3$ are as defined earlier, in a suitable inert organic solvent at a temperature of from 0° – 100° C. for from a few minutes to 20 hours. In a preferred embodiment of the method, the solvent is dry methylene chloride, the reaction temperature is less than 35° C., and the reaction time is 2 to 6 hours.

The starting 3-[2-(4-aminopiperazin-1-yl)ethyl]indoles are prepared by converting known indoles of the formula:

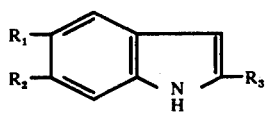

to the corresponding 3-(indolyl)glyoxalyl halides of the formula

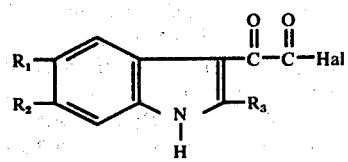

by the method of Speeter et al., J. Am. Chem. Soc., 76, 6209 (1954).

The intermediates so prepared are reacted with N-nitrosopiperazine at a temperature between −10° to 100° C. to give the corresponding 3- 1-(indol-3-ylglyoxyloyl)-4-nitrosopiperazine of the formula:

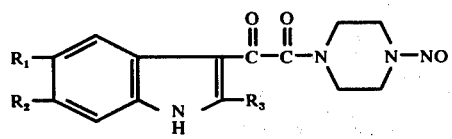

This reaction may or may not be carried out in a solvent or mixture of solvents. An added inorganic base such as potassium carbonate, or an organic base such as triethylamine, may be used to bind the hydrogen halide liberated during the course of the reaction; an added base is optional because the N-nitrosopiperazine can serve as the hydrogen ion acceptor.

Preferably, the reaction is carried out by adding the 3-(indolyl)glyoxalyl halide to a chloroform and water mixture containing the N-nitrosopiperazine and potassium carbonate while maintaining the temperature at 20°–25° C. over a span of from 1 minute to 60 minutes. This affords the crude 3-[1-(indol-3-glyoxyloyl)]-4-nitrosopiperazine in a nearly quantitative yield. With certain acide sensitive indoles such as when R$_1$ and R$_2$ are methoxy and R$_3$ is methyl, it may be advantageous to combine the first two steps of this method in one reaction vessel without isolating the sensitive glyoxalyl halide intermediate. For example, a mixture of 5,6-dimethoxy-2-methylindole and potassium carbonate in chloroform is treated with oxalyl chloride at −5° C. and the resulting glyoxalyl chloride is reacted in situ with N-nitrosopiperazine to produce the corresponding 3-[1-(indol-3-glyoxyloyl)]-4-nitrosopiperazine intermediate.

Reduction of this nitroso intermediate with an alkali metal hydride for a half hour to 24 hours produces the desired 3-[2-(4-aminopiperazin-1-yl)ethyl]indole starting compounds. This reduction is carried out in an organic solvent which is inert under the conditions of the reaction, for example, in ether, tetrahydrofuran, or 1,2-dimethoxyethane and at a temperature ranging from −10° C. to the boiling point of the solvent. In a preferred embodiment of the reaction, lithium aluminum hydride is used as the reducing agent, 1,2-dimethoxyethane is the solvent, and the mixture is refluxed to produce the indole in a nearly quantitative yield.

The compounds of this invention are useful as antihypertensive agents due to their ability to depress blood pressure in mammals. Antihypertensive activity was measured in the spontaneous hypertensive rat by the indirect tail cuff method described in A. Schwartz, Ed., *Methods in Pharmacology*, Vol. I, page 135, Appleton-Century Crofts, New York, New York, 1971.

In a standard 3 day test, according to this procedure, systolic blood pressure readings were made at 0 time (control) on days 1 and 3. Dosing was orally at 100 mgs/kg at 0 hour on days 1, 2 and 3 on groups of 6 animals per test. Activity was determined by comparison of the treated host's blood pressure values with the 0 time (control) blood pressure readings. A value of −15 mm Hg or more is considered significant.

The antihypertensive activity in this test of some of the compounds of the invention is illustrated in Table I.

Table I

| Compound | Day 1 mm Hg | Day 3 mm Hg |
|---|---|---|
| 1 [1-(indol-3-ylethyl)piperazin-4-yl]-3-phenylurea | −47 | −77 |
| 1-[1-(indol-3-ylethyl)piperazin-4-yl]-3-m-tolylurea | −45 | −78 |
| 1-[1-(indol-3-ylethyl)piperazin-4-yl]-3-cyclohexylurea | −46 | −44 |
| 1-[1-(5,6-dimethoxy-2-methyl-indol-3-ylethyl)piperazin-4-yl]-3-phenylurea | −36 | −38 |
| 1-[1-(indol-3-ylethyl)piperazin-4-yl]-3-p-fluorophenylurea | −13 | −35 |
| 1-[1-(indol-3-ylethyl)piperazin-4-yl]-3-p-chlorophenylurea | −12 | −54 |

Effective quantities in the range of from 0.1–100 mg/kg of body weight of any of the pharmacologically active 1-[1-(indol-3-ylethyl)-piperazin-4-yl]-3-substituted ureas may be administered to a patient by any one of the various methods, for example, orally as in capsules or tablets, parenterally in the form of sterile solutions or suspensions, and in some cases intravenously in the form of sterile solutions. The preferred route of administration is oral.

The active compounds of the present invention may be orally administered to a patient, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit contains between 0.1–100 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, primogel, cornstarch and the like; a lubricant such as magnesium stearate or sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For parenteral administration, the carrier or excipient may be a sterile, parenterally acceptable liquid; e.g., water or a parenterally acceptable oil; e.g., arachis oil contained in ampules.

Acids useful for preparing the physiologically tolerable acid addition salts of the invention include inorganic acids such as hydrochloric, hydrobromic, sulfuric, nitric, phosphoric and perchloric acids, as well as organic acids such as oxalic, tartaric, citric, acetic, succinic, maleic and ethane disulfonic acids.

EXAMPLE 1

A stirred solution of 6.13 g of 3-[2-(4-aminopiperazin-1-yl)ethyl]indole and 3.53 g of phenylisocyanate in 100 ml. of dry benzene is refluxed for 6 hours and then allowed to stand at ambient temperature overnight. Ether is added slowly to promote crystallization. The solid product is filtered, washed with ether and dried. The solid is recrystallized twice from a dimethylformamide water mixture to give crystals m.p. 168°–171° C. of 1-[1-(indol-3-ylethyl)piperazin-4-yl]-3-phenylurea.

Analysis: Calculated for $C_{21}H_{25}N_5O$: 69.40% C; 6.93% H; 19.27% N. Found: 69.98% C; 6.97% H; 19.45% N.

EXAMPLE 2

4.0 g of p-tolylisocyanate are added dropwise to a stirred solution of 6.13 g of 3-[2-(4-aminopiperazin-1-yl)-ethyl]indole in 100 ml. of dry methylene chloride while maintaining the reaction temperature below 35° C. After three hours at ambient temperature, ether is added to promote precipitation. The precipitate is filtered, washed with ether, and dried. The resulting solid is recrystallized twice from a methanol and water mixture to give 1-[1-(indol-3-ylethyl)piperazin-4-yl]-3-p-tolylurea, m.p. 201°–203° C.

Analysis: Calculated for $C_{22}H_{27}N_5O$: 70.00% C; 7.21% H; 18.55% N. Found: 69.64% C; 7.31% H; 18.58% N.

EXAMPLES 3–7

Following the manipulative procedure described in Example 2 and substituting for the p-tolylisocyanate the appropriate $R_4$ isocyanate, there are produced the 1-[1-(indol-3-ylethyl)piperazin-4-yl]-3-$R_4$ ureas listed in Table II.

Table II

| Ex. | $R_4$ | Recryst'n Solvent | M.P.° C. | | % C | % H | % N |
|---|---|---|---|---|---|---|---|
| 3 | p-fluorophenyl | Ethanol +H₂O | 203–205 | Calc. | 66.13 | 6.34 | 18.36 |
|   |   |   |   | Found | 65.96 | 6.30 | 18.22 |

Table II-continued

| Ex. | R₄ | Recryst'n Solvent | M.P.° C. | | %C | %H | %N |
|---|---|---|---|---|---|---|---|
| 4 | p-chlorophenyl | Ethyl Acetate | 212–214 | Calc. Found | 63.38 63.25 | 6.07 5.98 | 17.60 17.50 |
| 5 | p-nitrophenyl | Ethanol +H₂O | 206–208 | Calc. Found | 61.75 61.71 | 5.92 5.92 | 20.57 20.23 |
| 6 | cyclohexyl | Ethanol +H₂O | 178–180 | Calc. Found | 68.25 68.55 | 8.46 8.55 | 18.95 18.72 |
| 7 | ethyl | Ethyl Acetate | 196–199 | Calc. Found | 64.74 64.40 | 7.99 7.93 | 22.20 21.88 |

EXAMPLE 8

3.34 g of m-tolylisocyanate are added dropwise to a stirred solution of 6.13 g of 3-[2-(4-aminopiperazin-1-yl)ethyl]indole in 100 ml. of dry methylene chloride while maintaining the reaction temperature below 35° C. After 2 hours a fine precipitate appears, 50 ml. of ether are added and stirring is continued for 3 additional hours. More ether is added and the product is filtered and washed with ether. The solid product is recrystallized from an ethanol and water mixture to give white flakes, m.p. 186°–188° C. of 1-[1-(indol-3-ylethyl)piperazin-4-yl]-3-m-tolylurea.

Analysis: Calculated for $C_{22}H_{27}N_5O$: 70.00% C; 7.21% H; 18.55% N. Found: 70.21% C; 7.25% H; 18.45% N.

By following essentially the same procedure, substituting m-trifluoromethylphenylisocyanate for m-tolyliscyanate produces 1-[1-(indol-3-ylethyl)piperazin-4-yl]-3-m-trifluoromethylphenylurea.

EXAMPLE 9

3.5 g of phenylisocyanate are added dropwise to a stirred solution of 7.78 g of 3-[2-(4-aminopiperazin-1-yl)ethyl]-5,6-dimethoxy-2-methylindole in 100 ml. of dry methylene chloride while maintaining the reaction temperature below 35° C. After 2 hours, 50 ml. of ether are added, the product is filtered and washed with ether. The product is recrystallized from ethyl acetate to give a white solid, m.p. 170°–173° C. of 1-[1-(5,6-dimethoxy-2-methylindol-3-ylethyl)piperazin-4-yl]-3-phenylurea.

Analysis: Calculated for $C_{24}H_{31}N_5O_3$: 66.79% C; 6.95% H; 15.57% N. Found: 66.60% C; 7.11% H; 15.92% N.

By following essentially the same procedure but starting with (a) 3-[2-(4-aminopiperazin-1-yl)ethyl]-2-methylindole and 3,5-dimethoxyphenylisocyanate; (b) 3-[2-(4-aminopiperazin-1-yl)ethyl]-2-ethylindole and butylisocyanate; and (c) 3-[2-(4-aminopiperazin-1-yl)ethyl]-5,6-dimethoxyindole and 3,4,5-trimethoxyphenylisocyanate, it is possible to obtain (a) 1-[1-(2-methylindol-3-ylethyl)piperazin-4-yl]-3-(3,5-dimethoxyphenyl)urea; (b) 1-[1-(2-ethylindol-3-ylethyl)-piperazin-4-yl]-3-butylurea; and (c) 1-[1-(5,6-dimethoxyindol-3-ylethyl)piperazin-4-yl]-3-(3,4,5-trimethoxyphenyl)urea, respectively.

We claim:

1. A method of reducing hypertension which comprises orally or parenterally administering to a patient in need of such treatment an effective amount of an active compound of the formula

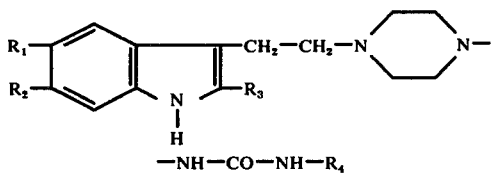

—NH—CO—NH—R₄ wherein $R_1$ and $R_2$ are hydrogen or alkoxy of from 1 to 3 carbon atoms; $R_3$ is hydrogen or alkyl of from 1 to 3 carbon atoms; and $R_4$ is alkyl of from 1 to 4 carbon atoms, cycloalkyl of from 3 to 8 carbon atoms, phenyl, or phenyl mono-, di-, or tri-substituted by halogen, alkyl of from 1 to 3 carbon atoms, alkoxy of from 1 to 2 carbon atoms, trifluoromethyl or nitro; or a physiologically tolerable acid addition salt thereof.

2. The method defined in claim 1 wherein the active compound is 1-[1-(indol-3-ylethyl)piperazin-4-yl]-3-ethylurea or a physiologically tolerable acid addition salt thereof.

3. The method defined in claim 1 wherein the active compound is 1-[1-(indol-3-ylethyl)piperazin-4-yl]-3-phenylurea or a physiologically tolerable acid addition salt thereof.

4. The method defined in claim 1 wherein the active compound is 1-[1-(indol-3-ylethyl)piperazine-4-yl]-3-p-fluorophenylurea or a physiologically tolerable acid addition salt thereof.

5. The method defined in claim 1 wherein the active compound is 1-[1-(5,6-dimethoxy-2-methylindol-3-ylethyl)piperazine-4-yl]-3-phenylurea or a physiologically tolerable acid addition salt thereof.

6. An orally administrable composition for reducing hypertension which consists essentially of a pharmaceutically acceptable carrier and from about 0.1–100 milligrams of the active compound defined in claim 1.

7. An orally administrable composition as defined in claim 6 wherein the active compound is 1-[1-(indol-3-ylethyl)piperazin-4-yl]-3-ethylurea or a physiologically tolerable acid addition salt thereof.

8. An orally administrable composition as defined in claim 6 wherein the active compound is 1-[1-(indol-3-ylethyl)piperazin-4-yl]-3-phenylurea or a physiologically tolerable acid addition salt thereof.

9. An orally administrable composition as defined in claim 6 wherein the active compound is 1-[1-(indol-3-ylethyl)piperazin-4-yl]-3-p-fluorophenylurea or a physiologically tolerable acid addition salt thereof.

10. An orally administrable composition as defined in claim 6 wherein the active compound is 1-[1-(5,6-dimethoxy-2-methylindol-3-ylethyl)piperazin-4-yl)-3-phenylurea or a physiologically tolerable acid addition salt thereof.

* * * * *